(12) United States Patent
Sacco et al.

(10) Patent No.: US 8,489,419 B2
(45) Date of Patent: *Jul. 16, 2013

(54) TRANSPORTATION MODE DETERMINATION IN NON-MASS CASUALTY TRIAGE

(75) Inventors: William J. Sacco, Bel Air, MD (US); D. Michael Navin, Bel Air, MD (US)

(73) Assignee: ThinkSharp, Inc., Towson, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/010,495

(22) Filed: Jan. 20, 2011

(65) Prior Publication Data

US 2011/0313783 A1 Dec. 22, 2011

Related U.S. Application Data

(63) Continuation-in-part of application No. 10/944,110, filed on Sep. 16, 2004, now Pat. No. 7,899,682, which is a continuation-in-part of application No. 10/385,829, filed on Mar. 11, 2003, now Pat. No. 7,761,309, and a continuation-in-part of application No. PCT/US03/08881, filed on Mar. 21, 2003.

(60) Provisional application No. 61/296,800, filed on Jan. 20, 2010, provisional application No. 60/367,527, filed on Mar. 22, 2002, provisional application No. 60/406,225, filed on Aug. 25, 2002, provisional application No. 60/503,530, filed on Sep. 16, 2003.

(51) Int. Cl.
*G06Q 10/00* (2012.01)
*G06Q 50/00* (2012.01)

(52) U.S. Cl.
USPC .................................. 705/2; 705/3; 235/385

(58) Field of Classification Search
USPC ............................................................ 705/2
See application file for complete search history.

(56) References Cited

U.S. PATENT DOCUMENTS 5,809,477 A 9/1998 Pollack
5,964,065 A 10/1999 Migurski et al.
(Continued)

FOREIGN PATENT DOCUMENTS

JP 10-116023 5/1998
JP 11-95648 4/1999

OTHER PUBLICATIONS

Champion et al., A Revision of the Trauma Score, 1989 The Williams & Wilkins Co., vol. 29, No. 5, The Journal of Trauma.*
(Continued)

*Primary Examiner* — Hiep V Nguyen
(74) *Attorney, Agent, or Firm* — Blank Rome LLP

(57) ABSTRACT

Transportation mode determination in non-mass casualty triage is provided and involves receiving, from incident personnel at a casualty scene, patient screening information for a victim or victims at the casualty scene. Location screening information for the victim or victims is also established and received. Victim eligibility for Medevac transport is determined by logically factoring the patient screening information and the location screening information. The determination can be performed by computer implemented decision logic. In addition to determining eligibility of the victim or victims for Medevac transport, transportation mode determination (e.g., what type of transportation) can be established for those determined eligible, determination of whether to transport to a trauma center or care facility, determination/selection of a specific trauma center or care facility for treatment, and/or a determination of an order of treatment, or transport for treatment, for each of the victims.

20 Claims, 7 Drawing Sheets

U.S. PATENT DOCUMENTS

| | | | |
|---|---|---|---|
| 6,305,605 | B1 | 10/2001 | Goetz et al. |
| 6,383,135 | B1 | 5/2002 | Chikovani et al. |
| 6,416,480 | B1 | 7/2002 | Nenov |
| 6,499,658 | B2 * | 12/2002 | Goetz et al. ............ 235/385 |
| 6,804,656 | B1 | 10/2004 | Rosenfield et al. |
| 7,761,309 | B2 | 7/2010 | Sacco |
| 7,899,682 | B2 | 3/2011 | Sacco |
| 2002/0011518 | A1 | 1/2002 | Goetz et al. |
| 2002/0153413 | A1 | 10/2002 | Piatek et al. |

OTHER PUBLICATIONS

Steger, M.R., "Emergency medical services prehospital triage," J. Emergency Care, Apr. 3, 2003, http://www.emsmagazine.com; 8 pages.

START, "Simple triage and rapid treatment," Student Manual; 23 pages.

Mass Casualty Incident Program, "Initial triage training," sponsored by A.E.M.S., Nov. 27, 2002; http://www.ge.maricopa.edu, 30 pages.

MS, "Mass casualty incidents and start triage," Nov. 27, 2002; http://www.co.broward.fl.us; 14 pages.

Disaster Response: principles of preparation and coordination, "Triage," Apr. 3, 2003, Chapter 8, http://216.202,128.19/dr/disaster response.nsf.; 23 pages.

Disaster Medical System, "Triage System, Function 7: Coordination of pre-hospital emergency services," Nov. 27, 2002, http://www.mvemsa.com; 4 pages.

EMMCO West, "START's the choice in the EMMCO West Region," Nov. 27, 2002, http://www.emmco.org; 2 pages.

CERT-LA S.T.A.R.T, "Simple triage and rapid treatment," CERT-Los Angeles, Nov. 27, 2002, http://www.cert-lacom; 8 pages.

Weiser, Benjamin, "Medicine's Reliability Rivaled by Software," The Washington Post, Washington DC, Jan. 1, 1992, p.a.08.

Strosberg, Martin A., "Intensive Care Units in the Triage Mode: An Organizational Perspective," Hospital and Health Services Administration, Spring 1991; p. 95.

Howard R. Champion, F.A.C.S., A Revision of the Trauma Score, The Journal of Trauma, 1989, vol. 29, No. 5, pp. 623-629.

* cited by examiner

Survival Probability After Applying Injury, MOI and Physiological Screens

| RPM | 0-7 | 8-14 | 15-54 | 55-74 | 75+ | Total |
|---|---|---|---|---|---|---|
| 0 | 7.87% | 7.41% | 4.24% | 5.22% | 1.39% | 4.67% |
| 1 | 75.00% | 0.00% | 16.13% | 10.53% | 0.00% | 18.00% |
| 2 | 50.00% | 0.00% | 20.29% | 7.69% | 37.50% | 20.43% |
| 3 | 37.50% | 11.11% | 38.55% | 6.25% | 13.33% | 29.77% |
| 4 | 53.33% | 56.25% | 53.18% | 58.62% | 13.64% | 50.59% |
| 5 | 69.70% | 58.33% | 60.53% | 47.54% | 21.05% | 55.78% |
| 6 | 81.58% | 62.50% | 69.81% | 48.48% | 38.46% | 65.38% |
| 7 | 92.96% | 89.74% | 81.80% | 63.83% | 41.54% | 77.86% |
| 8 | 92.37% | 86.54% | 87.96% | 69.47% | 55.95% | 83.09% |
| 9 | 100.00% | 98.50% | 93.19% | 82.05% | 67.91% | 90.48% |
| 10 | 99.76% | 99.65% | 97.48% | 95.81% | 87.68% | 95.85% |
| 11 | 99.47% | 99.50% | 98.88% | 96.25% | 87.56% | 97.21% |
| 12 | 99.72% | 100.00% | 99.56% | 98.27% | 95.22% | 98.69% |

Survival Probability After Applying Injury, MOI and Physiological Screens

| RPM | 0-7 | 8-14 | 15-54 | 55-74 | 75+ | Total |
|---|---|---|---|---|---|---|
| 0 | 7.87% | 7.41% | 4.24% | 5.22% | 1.39% | 4.67% |
| 1 | 75.00% | 0.00% | 16.13% | 10.53% | 0.00% | 18.00% |
| 2 | 50.00% | 0.00% | 20.29% | 7.69% | 37.50% | 20.43% |
| 3 | 37.50% | 11.11% | 38.55% | 6.25% | 13.33% | 29.77% |
| 4 | 53.33% | 56.25% | 53.18% | 58.62% | 13.64% | 50.59% |
| 5 | 69.70% | 58.33% | 60.53% | 47.54% | 21.05% | 55.78% |
| 6 | 81.58% | 62.50% | 69.81% | 48.48% | 38.46% | 65.38% |
| 7 | 92.96% | 89.74% | 81.80% | 63.83% | 41.54% | 77.86% |
| 8 | 92.37% | 86.54% | 87.96% | 69.47% | 55.95% | 83.09% |
| 9 | 100.00% | 98.50% | 93.19% | 82.05% | 67.91% | 90.48% |
| 10 | 99.76% | 99.65% | 97.48% | 95.81% | 87.68% | 95.85% |
| 11 | 99.47% | 99.50% | 98.88% | 96.25% | 87.56% | 97.21% |
| 12 | 99.72% | 100.00% | 99.56% | 98.27% | 95.22% | 98.69% |

TRANSPORTATION MODE DETERMINATION IN NON-MASS CASUALTY TRIAGE

CROSS REFERENCE TO RELATED APPLICATIONS

This application claims benefit of priority of U.S. Provisional Application No. 61/296,800, filed Jan. 20, 2010. This application is also a continuation-in-part of U.S. application Ser. No. 10/944,110, filed Sep. 16, 2004; which application claims benefit of priority of U.S. Provisional Application No. 60/503,530, filed Sep. 16, 2003.

U.S. application Ser. No. 10/944,110, filed Sep. 16, 2004, is a continuation-in-part of U.S. application Ser. No. 10/385,829, filed Mar. 11, 2003 (now U.S. Pat. No. 7,761,309); which application claims benefit of priority of U.S. Provisional Application Ser. No. 60/367,527, filed Mar. 22, 2002, and of U.S. Provisional Application Ser. No. 60/406,225, filed Aug. 25, 2002.

U.S. application Ser. No. 10/944,110, filed Sep. 16, 2004, is also a continuation-in-part of International Application No. PCT/US03/08881, filed Mar. 21, 2003; which application claims benefit of priority of U.S. Provisional Application Ser. No. 60/367,527, filed Mar. 22, 2002, and of U.S. Application Ser. No. 60/406,225, filed Aug. 25, 2002. The contents of all of the above-identified related applications are incorporated herein by reference.

FIELD OF THE INVENTION

The present invention relates generally to single and multiple casualty triage, and mass and non-mass casualty triage; and more particularly to a method and system for transportation mode determination non-mass casualty triage.

BACKGROUND OF THE INVENTION

A multiple or mass casualty incident can generally be defined as an emergency or disaster where the number of patients or victims exceeds or taxes available resources, or where resource access is restricted or limited or where resources have to be staged. In contrast to routine emergencies, efficiently responding to a mass casualty incident requires triage protocol and procedures for effectively allocating the limited resources.

Triage, from the French verb trier, means to sort, and is the foundation of mass or multiple casualty management. Traditionally, medical attention and transportation to a next level of care is given first to those with the most urgent conditions. While this is appropriate in circumstances when resources are available for the immediate care of all victims, this does not necessary utilize resources most effectively when resources are limited.

The goal in the most widely used methods of mass casualty triage is typically to "do the greatest good for the greatest number". This goal is not very explicit. A more tangible and measurable goal is to maximize the saving of lives. Achieving this explicit goal requires the maximum utilization of transport and treatment resources in consideration of the timing and availability of those resources, the severity of the injuries of the victims, and their deterioration should care and transport to the next level of care be delayed as a result of resource limitations.

Accordingly, triage shall be referred to herein as an organized evaluation of all casualties to prioritize treatment and/or transport of the casualties. Further, triage includes the consideration for the availability and timing of treatment and transport resources.

When casualties are generated in large numbers, as in a mass casualty incident, local medical resources can easily be overwhelmed. The scene is often in chaos, and the response can be disorganized. As such, the efficient use of resources is compromised, with emergency response personnel left to do the best they can. There is no single, standard, or universal method of triage to support these efforts. The present invention provides such a standard, by providing a method and system of triage for determining an order of treatment, or transport for treatment, for victims of a mass casualty incident, to maximize the number of survivors of the mass casualty incident.

Non-mass casualty triage generally refers to a situation where resources are generally immediately available for all casualties of an incident. Non-mass casualty triage could involve multiple casualties, or just one casualty. In either event, transportation modes are immediately available, as are all required levels of trauma treatment, to adequately and fully triage all casualties of the incident. So, the question is not how to best distribute limited resources in limited time, as it is in mass casualty triage; rather, in non-mass casualty triage, the question becomes how to most efficiently use the choice of resources available, and how to best benefit from the additional time (more than in mass casualty triage), that allows for a more thorough casualty assessment.

For example, what is needed in transportation mode determination in non-mass casualty triage are efficient determinations that significantly reduce overtriage while maintaining target levels of undertriage. The present invention provides such a method and system.

SUMMARY OF THE INVENTION

The present invention is a method and system of triage for determining an order of treatment, or transport for treatment, for victims of a mass casualty incident, to maximize the number of survivors of the mass casualty incident. The present invention can employ real-time incident information, or employ simulated, evidence based information.

Further, in another aspect of the invention, a method and system of transportation mode determination in non-mass casualty triage is presented, providing an efficient determination of transportation mode (e.g., what type of transportation to use for victim transport to a trauma center or care facility), a determination of whether to transport a victim to a trauma center or care facility, and/or a determination/selection of a specific trauma center or care facility for treatment of the victim or victims.

First, the present invention is a method and system of triage that determines a severity score for each patient quickly and accurately, and provides a treatment prioritization plan that considers and includes all casualties and all available resources to maximize total survivability, in some cases resulting in as many as seven times the survivability of current triage methods. The present invention includes a score-based mathematical algorithm for resource-constrained triage that explicitly maximizes the saving of lives in consideration of victim injury severity, victim survival probabilities, victim deterioration rates, and resource availability.

The present invention provides a prioritization plan that identifies a specific number of casualties, and the severity score of each casualty, for treatment and/or transport in any given period of resource availability. The computer model of the present invention solves instantaneously, even for large-scale casualty incidents, and is dynamic, as the model can be solved and resolved in real time as victims, resources, and conditions change.

In one aspect of the present invention, a method of mass casualty triage establishes a casualty severity score for each of a plurality of victims, then determines an order of treatment for each of the plurality of victims through consideration of the casualty severity score and resource availability. Any of a number of casualty scoring techniques, either known or to be developed, could be employed. Determining an order of treatment for each of the plurality of victims could involve mathematical or analytical programming techniques, such as but not limited to dynamic or linear programming formulations. The method could further calculate a number of expected survivors of a respective casualty incident.

In another aspect, determining an order of treatment, or transport for treatment, of the plurality of casualties could consider resource availability, the casualty severity scores, and casualty severity score deterioration rates resulting from time periods of transport and/or treatment delay. The casualty severity score deterioration rates, or victim deterioration-with-time rates, could be assumed, could be data-based, or could be determined through consideration of factors selected from one or more of an availability of state-of-the-art, or lesser levels of treatment; a cause of a casualty incident; a type of anatomic injury incurred by the victim; an age of the victim; treatment available at the incident scene; treatment available at other facilities; distances to the other facilities; and, facilities or equipment available for performance of casualty management.

In another aspect of the present invention, a triage method first assesses a respiratory rate, pulse rate, and best motor response for each of a plurality of casualties and assigns a coded value for each based on the assessment. A severity score is then established for each of the plurality of casualties by summing the coded values. Based on the total score, a survival probability is assigned to each severity score. Then, mathematical or analytical programming techniques are used to determine an order of treatment for each of the plurality of casualties.

Second, in another aspect of the present invention, a card, chart, table graph, is provided that illustrates the results of the triage methods of the present invention summarized above, as directed to simulated casualty incidents. The card provides quick, practical, and suboptimal maximization of survivability, without requiring the use of computers or the calculation of algorithms in response to a casualty incident because the ordering is determined prior to the respective casualty incident. In this aspect, the ordering of treatment or transport, for display on the card, chart, table or graph, can be determined by running triage simulations of random or uniformly generated victim distributions and resource constraints, in accordance with the triage methods summarized above. Or, the order of treatment can be determined by employing data mining, pattern recognition, greedy algorithm and/or other exploratory analyses.

Third, in a further aspect of the invention, a method and system of transportation mode determination in non-mass casualty triage is provided and involves receiving, from incident personnel at a casualty scene, patient screening information for a victim or victims at a casualty scene. Additionally, location screening information for the victim or victims at the casualty scene is established and received. The patient screening information and location screening information can be input into a computer. Then, victim eligibility for Medevac transport is determined by logically factoring the patient screening information and the location screening information. The determination can be performed by computer implemented decision logic, and the determination can be directed to either eligibility for air ambulance transport, or eligibility for transport by any medically equipped vehicle (whether air or ground).

The patient screening information can include one or more of a victim casualty severity score, a victim age adjusted casualty severity score, a victim survival probability rate, a type of trauma, an anatomic injury and a mechanism of injury. The location screening information includes one or more of a location of the victim, a proximity of the victim to Medevac transport mode options, proximity of the victim to a treatment facility as measured by transfer time required by transport mode options, and relative to the severity score deterioration-with-time rate.

In another aspect, if the victim is determined eligible for Medevac transport, the method and system can further determine a mode of Medevac transport; or if the victim is determined ineligible for Medevac transport, can further determine whether the victim is eligible for care at a trauma center or care facility. These determinations can logically factor one or more of a type of injury incurred by the victim, an age of the victim, an age adjusted RPM score, treatment available at the casualty scene, treatment available at other facilities, and physiologic characteristics of the victim and mechanism of injury.

As mentioned, the transportation mode determination in non-mass casualty triage can address single or multiple victims. Eligibility for Medevac transport, the mode of Medevac transport, whether the victim or victims are eligible for care at a trauma center or care facility, and/or and ordering of treatment, or transport for treatment, can be determined for each of the plurality of victims in accordance with the method and systems of the present invention.

In one embodiment of the invention, a method of transportation mode determination in non-mass casualty triage is performed by receiving, from incident personnel at a casualty scene, a casualty severity score for a victim at a casualty scene; assigning, or separately establishing, a survival probability for the casualty severity score based upon at least one characteristic of the respective victim or of an incident responsible for the victim; and assigning, or separately establishing, a casualty severity score deterioration-with-time rate based upon at least one characteristic of an availability of state-of-the-art, or lesser levels of treatment; a type of anatomic injury incurred by the victim; an age of the victim; a mechanism of injury; treatment available at the casualty scene; treatment available at other facilities; distances to the other facilities; and facilities or equipment available for performance of care. Then, at least the survival probability and the casualty severity score deterioration-with-time rate information is input into a computer; and computer implemented decision logic then determines victim eligibility for Medevac transport, wherein the determination logically factors the survival probability and the casualty severity score deterioration-with-time rate.

Additionally, if the victim is determined eligible for Medevac transport, another embodiment can further determine a mode of Medevac transport, where the determination logically factors one or more of a location of the victim, proximity of the victim to transport mode options, proximity of the victim to the treatment facility as measured by transfer time required by transport mode options relative to the severity score deterioration-with-time rate. If the victim is determined ineligible for Medevac transport, a further embodiment can further determine whether the victim is eligible for care at a trauma center or care facility, where the determination logically factors one or more of a type of injury incurred by the victim; an age of the victim; an age adjusted RPM score; treatment available at the casualty scene; treatment available at other facilities; physiologic characteristics of the victim and mechanism of injury.

The transportation mode determination in non-mass casualty triage aspect of the invention equally addresses the situation where a plurality of victims exist at the casualty scene, and determines eligibility for Medevac transport for each of each of the plurality of victims, in one embodiment by logically factoring the survival probability and the casualty severity score deterioration-with-time rate for each victim. Where a plurality of victims exist, the present invention can further determine an order of treatment, or transport for treatment, for all victims previously determined eligible for Medevac transport; in one embodiment by further receiving information indicative of triage resources available for the plurality of victims, and determining the order of treatment, or transport for treatment, by mathematically factoring the casualty severity score for each victim and the triage resources available for the plurality of victims.

BRIEF DESCRIPTION OF THE DRAWINGS

For the purpose of illustrating the invention, there is shown in the drawing one embodiment of the present invention; it being understood, however, that this invention is not limited to the precise arrangements and instrumentalities shown.

DETAILED DESCRIPTION OF THE INVENTION

Figure 1:
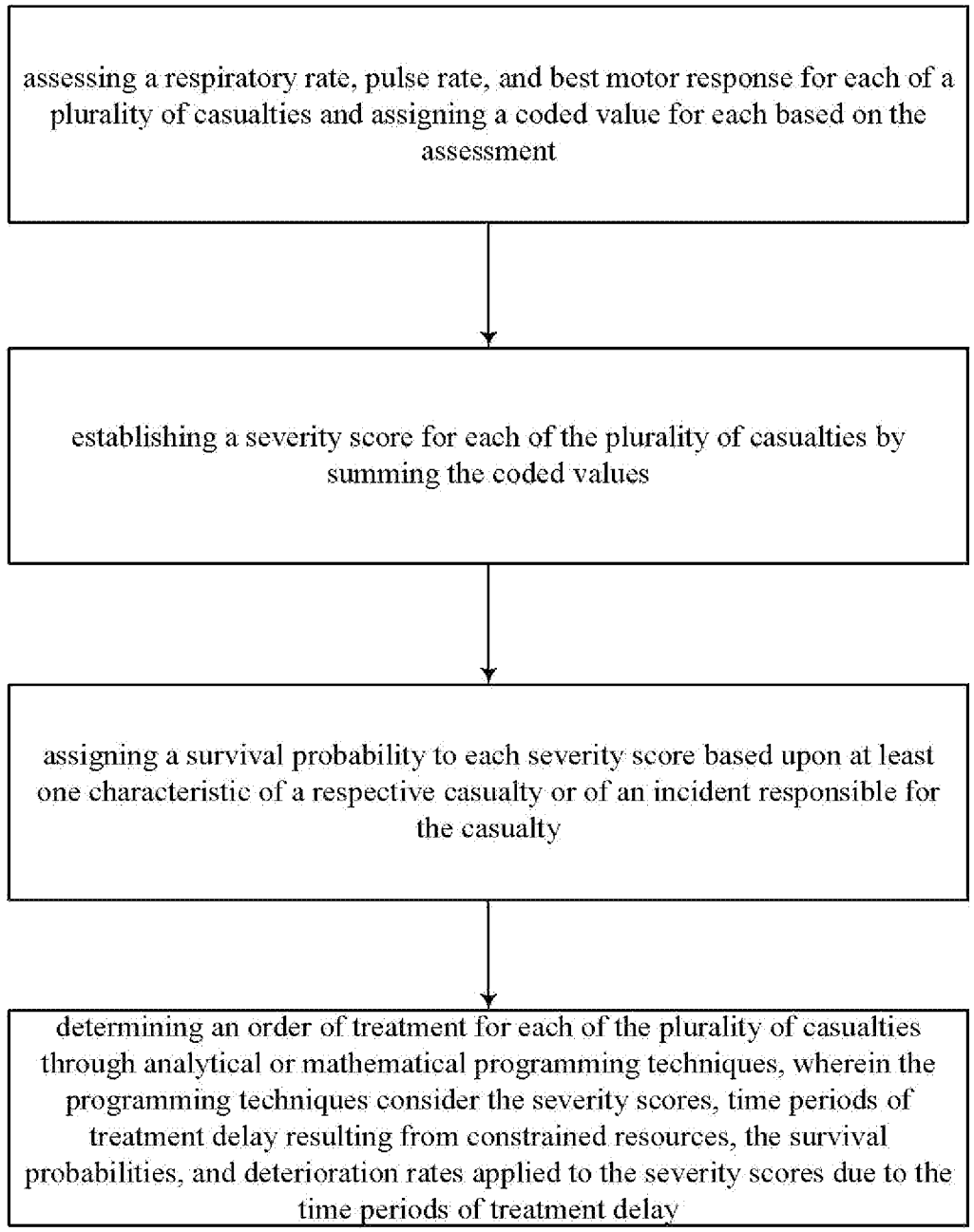
FIG. 1 is a flow diagram illustrating a method of triage in accordance with one embodiment of the present invention.

The present invention provides a method of managing triage for multiple and mass casualty incidents. Generally, the method of the present invention includes the following procedures:

1. Determining a casualty severity score for each victim; and
2. Determining a priority order of treatment for the victims.

The goal of the present invention is to maximize the expected number of survivors in any multiple or mass casualty or resource constrained triage incident. Achieving this goal requires, as resources become available, determining an order upon which victims will be treated, or upon which victims will be transported for treatment, or some combination thereof.

Accordingly, determining a priority order of treatment could occur at the incident scene, and be directed to an order of victim transport to a medical facility. Or, the priority order could be directed to an order of initial treatment at the incident scene, with or without further transport to a medical facility. Or, determining a casualty severity score for each victim, and determining an order of treatment, could occur at an emergency room, or other medical facility intake area, to facilitate optimal triage management at a more specific and localized area remote from an casualty incident scene.

In a catastrophic event, a multiple or mass casualty incident, or any casualty incident where transport and treatment resources are limited, a major issue confronted by triage personnel is that not all of the injured can receive state-of-art treatment instantaneously due to limited resources, either at the incident scene or at further echelons of care, such as holding areas, emergency departments, and resuscitation bays. For the foregoing reasons, the present invention contemplates use in any location, and for any incident, where optimal triage management procedures would result in maximizing victim survival.

For purposes of resolving a triage problem, the present invention recognizes time periods, each time period represented by an amount of resources available for treatment and/or transport of casualties. Due to the likely limitation on resources, certain casualties may wait one or more time periods before receiving treatment by or transport to upper echelons of care. Time periods may be of variable length, and the resources available during any one time period may or may not be equal to the resources available during other time periods. The present invention recognizes the importance of full and efficient utilization of resources across all time periods, and contemplates employment of certain problem solving methods to ensure full and efficient utilization of resources across all time periods. For instance, if time period length is essentially defined by emergency transport time in route to a certain upper echelon care facility, the present invention could employ problem solving techniques such as Dijkstra's method to minimize time in route.

In one aspect of the present invention, the casualty severity scoring method used is "RPM," a method using coded values of a casualty's Respiratory rate, Pulse rate, and best Motor response (a measure of neurological status). It is envisioned that the present invention could employ other methods of casualty scoring, or variations of the RPM model detailed herein, as various scoring applications, either known or to be developed, could easily be adapted to the broad concepts of the present invention. By way of example, the present invention could alternatively incorporate Revised Trauma Score (RTS), the recognized triage standard of the American College of Surgeons. Further, several other abbreviated physiologic severity scores exist and could be incorporated into the present invention, including RPV (based on respiratory rate, pulse rate, and best verbal response), body-region-injury dependent RPV, body-region-injury dependent scores (based on respiratory rate and pulse rate), the Glasgow Coma Scale and best motor response. Also, a scoring methodology could be developed and used based upon the assessment methods currently employed in START.

In another aspect of the present invention, the treatment and triage priorities are then determined from analytical, mathematical, and/or optimization techniques, such as dynamic programming or linear programming, and can incorporate, for greater precision, one or more of data-based estimates of casualty survival probabilities and victim deterioration-with-time rates. The data could be accumulated from previous injury scene data for trauma patients, such as trauma registries, or other mass casualty incidents, or could be estimated based on experts' subjective opinions, with survival probabilities and deterioration rates determined using standard statistical methods.

If incorporating casualty survival probabilities and/or deterioration-with-time rates into the model, a probability or rate could be determined for and used with each of the RPM values. If desired, for greater precision, the survival probability or deterioration rate could be determined using data that considers any one or more of a variety of factors, such as but not limited to an availability of state-of-the-art, or lesser levels of treatment; a cause of or weapon used to create the mass casualty incident (such as a weapon of mass destruction, or a natural disaster); type of anatomic injury incurred by the casualty (such as blunt or penetrating injury, or trauma from blast, chemical, radiological or biological incident); age or age range of the casualty; treatment available at the incident scene, and/or at locations of higher echelons of care; distances to the higher echelons of care; and facilities or equipment available for performance of the casualty management itself. The above list of factors is exemplary, and not limiting, as the casualty survival probabilities and victim deterioration-with-time rates could be a work in progress, continually refined based upon ever-increasing data directed to the above-referenced factors, to other existing factors having available data, or to factors yet to be developed with consideration of the concepts of the present invention.

In another aspect of the present invention, either dynamic or linear programming can be used to determine a priority of treatment for the casualties, each operating irrespective of the specific factors chosen above. The dynamic and linear programming formulations are each directed to maximizing the number of victims saved across all time periods, subject to constraints on available resources in each time period and the number of victims of particular severity score available within each time period. The dynamic and linear programming approaches provide essentially the same optimal result, the difference being approach and method of solution. The present invention also envisions using other methods to determine treatment priorities, including heuristic methods, such as but not limited to search theory based solutions and greedy approaches operating to optimize the number of survivors.

For further precision, the dynamic and/or linear programming formulations could maximize the number of victims saved across all time periods by further considering a type of trauma experienced by the victim, a classification of the victim, and/or a type of care center appropriate for and available to the victim. For instance, specific embodiments could consider, in determining prioritization, that the victim has experienced blunt or penetrating trauma, or blast, chemical, radiological, or biological trauma. Considering the type of trauma experienced, in addition to and in conjunction with the consideration of severity score, could further aid the maximization of victims saved by optimizing the prioritizations determined. A class of the victim could consider age and/or previous health conditions of the victim, and incorporate same into the considerations above. For type of care center, the dynamic or linear programming could determine a priority of treatment based upon a further consideration of matching a type of injury to specific care centers and/or doctors appropriate for and available to the victim, to avoid inefficiencies possible when a victim is transported or received for treatment, but then cannot receive same because needed specialty care is not available at that time, or at that location.

In another aspect, the present invention also includes software to encapsulate the methods expressed herein, the software also providing management assistance for performance of each step of the respective method employed. The software would be compatible with standard personal and laptop computers, and compatible with mobile devices, such as PDAs (i.e. Personal Digital Assistants), presently existing or to be developed, the software providing management assistance and method capability at the incident scene, at one or more remote locations, or at any combination thereof.

In still another aspect of the present invention, triage strategy is determined by software at a central processing location, with coordinated programming by hand held devices located at the incident scene. This aspect employs fully automated dispatch, matching victims with transport and hospital resources through automated data communication. Alternatively, the methods of the present invention could be carried out using a command center approach, where two-way radios communicate necessary data to central control. Further, a simulation driven, rule based protocol could be established having control in the field. In the simulation driven approach, emergency personnel would arrive at a casualty event and quickly characterize the scene and the resources available (i.e., generally characterize a number and a severity of casualties in relation to resource availability, thereby determining a degree of resource constraint). Next, as individual victim assessment begins, the characterization of the entire event is associated with one of several (or more) protocols. The protocol provides direction regarding an order of treatment necessary to maximize total survivability for a given casualty event, and each protocol is pre-established based on simulations including certain assumptions, or facts, about the given casualty event. The quick characterization of the entire event guides the emergency personnel in a selection of a pre-established protocol most closely resembling the casualty incident at issue.

By way of example, the following describes certain aspects of the present invention:

RPM Scoring

RPM is the sum of coded values of respiratory rate (RR), pulse rate (PR), and best motor response (BMR). In one embodiment, the coded values are:

| RR: | 0, | 1-9, | 10-24, | 25-35, | 35+ |
|---|---|---|---|---|---|
| Coded Values | 0 | 1 | 4 | 3 | 2 |
| PR: | 0, | 1-40, | 41-60, | 61-120, | 120+ |
| Coded Values | 0 | 1 | 2 | 4 | 3 |
| BMR: | None, | Ext/Flex, | Withdraws, | Localizes, | Obeys Commands |
| Coded Values | 0 | 1 | 2 | 3 | 4 |

In this embodiment, RPM takes on integer values from zero (0) to twelve (12). RR is measured in breaths/minute, and is implemented by measuring breaths for fifteen (15) seconds and multiplying by four (4). PR is measured in beats/minute, and is implemented by measuring beats for fifteen (15) seconds and multiplying by four (4). BMR assesses the ability of the casualty to respond with movement to stimuli as follows:

Obeys Commands: This requires an ability to comprehend instructions given by verbal command. The casualty must perform the specific movement requested. The following could be a typical routine: the first verbal command is "raise your hand"; if the casualty does so, the assessment is Obeys Commands; if not, the second command is "squeeze my hand"; if the casualty does so, the assessment is Obeys Commands; if not, a painful stimulus, preferably a "nail bed" stimulus, is applied to try to produce a response.

Localizes pain: After painful stimulation, the casualty reaches and/or tries to remove the source of pain.

Withdraws: After painful stimulation, there is flexion of elbow, with rapid movement and no muscle stiffness, and the arm is drawn away from the trunk.

Flexion: After painful stimulation, the elbow flexes slowly accompanied by stiffness, and the forearm and hand remain held against the body.

Extension: After painful stimulation, the legs and arms extend. This movement is accompanied by stiffness and there is internal rotation of the shoulder and forearm.

None: No response to pain.

In one embodiment of the invention, the following is a sample calculation of RPM: If RR=16, PR=50, and BMR is "Obeys Commands", then the coded values are 4, 2, and 4 (from above), and the sum of the coded values (the RPM) equals ten (10).

Casualty Survival Probabilities

By way of example, in one embodiment of the present invention the following are the survival probabilities associated with each RPM value. The survival probabilities presented below are based upon data compiled from various hospital and state-wide trauma statistics involving thousands of casualties.

| RPM Value | Survival Probability |
| --- | --- |
| 12 | .992 |
| 11 | .985 |
| 10 | .970 |
| 9 | .970 |
| 8 | .910 |
| 7 | .830 |
| 6 | .720 |
| 5 | .570 |
| 4 | .410 |
| 3 | .270 |
| 2 | .160 |
| 1 | .090 |
| 0 | .052 |

Victim Deterioration-with-Time Rates

By way of example, in one embodiment of the present invention the following presents victim deterioration-with-time rates for casualties who remain at the incident scene and continue to receive first respondent treatment at most. The deterioration-with-time rates presented below are based upon interviews with trauma center personnel directed to experiences and statistics of trauma victims and their respective treatment.

| RPM values | Score Point Decrease/30 minutes |
| --- | --- |
| 11-12 | 1 ** |
| 8-10 | 1 |
| 5-7 | 2 |
| 3, 4 | 3 |
| 2 | 2 |
| 1 | 1 |
| 0 | 0 |

** For RPM values of 11-12, the score point decrease of one (1) occurs over two (2) thirty (30) minute time periods.

Note:
an example helps to interpret the table. A victim with a first assessment RPM value of eight (8) would have a value of seven (7) thirty (30) minutes after the first assessment, and a value of five (5) one (1) hour after the first assessment with an associated decrease in survival probability from .91 to .57.

Figure 2:
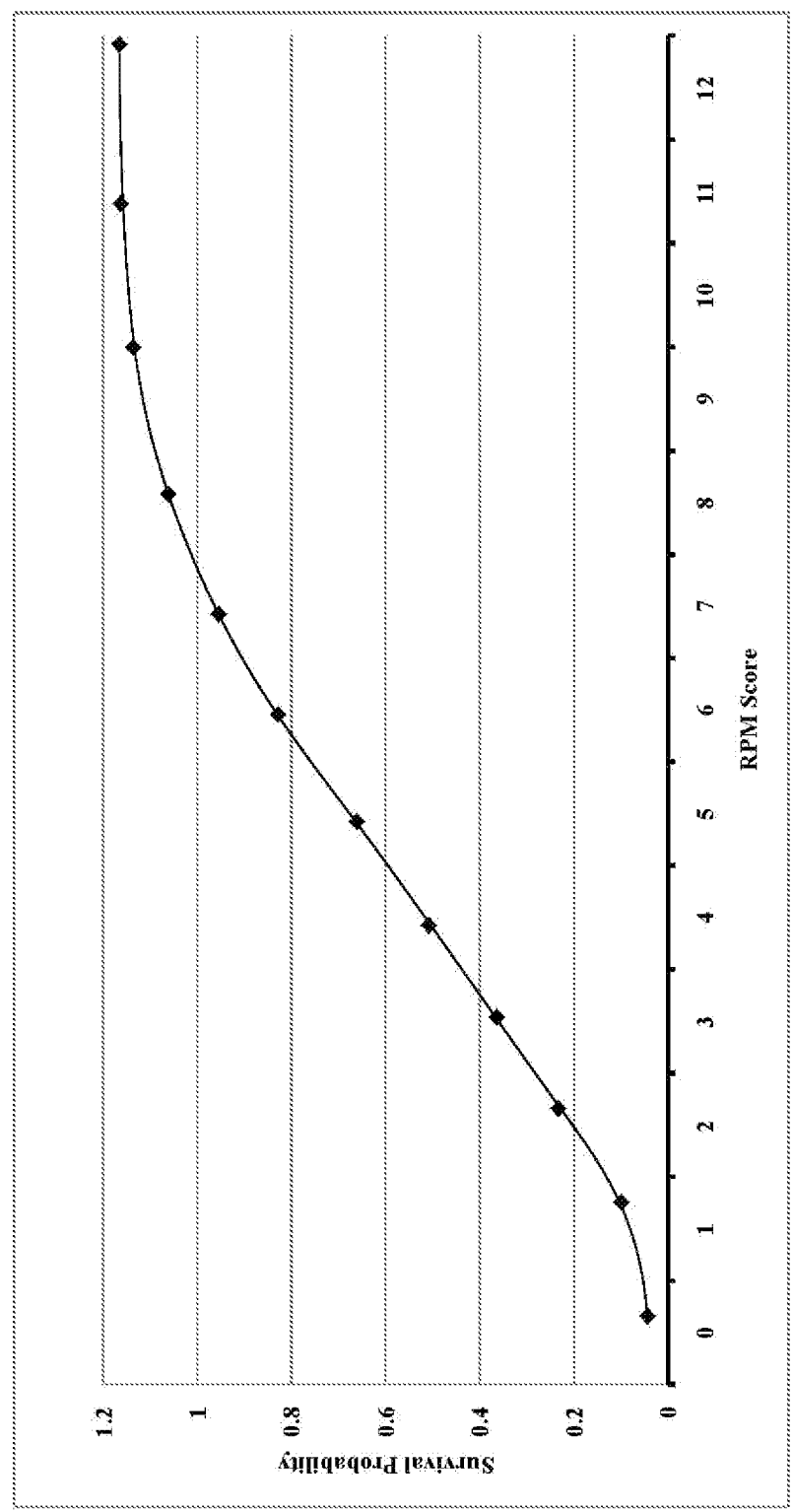
FIG. 2 is a graph illustrating a relationship between survival probability and casualty severity score in accordance with an embodiment of the present invention.

Casualty Survival Probability in Relation to Victim Deterioration-with-Time Rates FIG. 2 illustrates graphically the specific survival probabilities presented above in relation to respective RPM score. The plotted points of FIG. 2 create an "S"-shaped curve, the "S"-shaped curve including somewhat leveled-off survival probabilities at the high and at the low end of the RPM values, but demonstrating a substantial decrease in, or declining, survival probability between the RPM scores of approximately seven (7) and four (4). Combining this finding with the specific deterioration-with-time rates presented above, it can be seen that, over the entire range of RPM scores, there is a crucial and central range of rapid deterioration in survival probability for RPM scores between 7 and 4).

Determining Treatment and/or Transportation Prioritization

By way of continued example, in one embodiment of the present invention casualty prioritization for treatment and/or transportation is determined by combining: 1) RPM severity scoring and associated survival probability estimates; 2) victim deterioration-with-time rates for those casualties remaining at the incident scene and receiving only first-respondent treatment; and 3) dynamic programming and linear programming.

The RPM value is assessed for each casualty by first responders. The underlying assumption is that the human body responds in specific ways to trauma, depending on the severity of the trauma. More severe trauma results in physiological changes from normal which are greater than those associated with less serious trauma. As with all physiologically based severity scoring, the time interval between the trauma and the assessment can affect the severity score, since the response of body systems to trauma is not instantaneous, but graded over time. There is great value in serial assessments and the charting of changes in the value of assessments over time.

To complete the prioritization process, the dynamic or linear programming problem is solved, the formulation of the problem appearing below:

Stochastic Dynamic Programming Formulation

Let O (N)=Maximum Expected number of Survivors for N casualties in the event where N=($n_0, n_1, \ldots, n_k$); $n_i$=the number of victims with a severity score equal to i, where i=0 . . . k. The problem can then be formulated as a multidimensional, stochastic dynamic programming problem as follows:

$$O(N) = \underset{(STF)}{\text{maximum}} [\text{expected survivors (subset triaged first)} + O(N')]$$

where, STF=subset of patients selected for first transport and/or first treatment, and N'=($n_0', n_1', \ldots, n_k'$).

Notes on the formulation of this embodiment of the present invention:

1. The number of patients in the subset STF will correspond to the number of patients that can be treated by the resources in the next echelon of treatment available.
2. N' is a state vector which reflects the numbers of patients not included in the first group triaged and their predicted RPM values at the time of triage for the next group.
3. The mass casualty triage problem is a multistage problem with successive stages being a selection of a subset of patients for triage to the next echelon of care. The quantity inside the brackets [ ] gives the expected number of survivors for an arbitrary selection of the first patient set to be triaged (first term inside the brackets) plus the second term inside the brackets, which is the maximum expected number of survivors "for the remaining stages" given the casualty state (status) of the remaining (nontriaged) casualties at the time of next opportunity to triage. Accordingly, the quantity inside the brackets represents one arbitrarily triaged subset (the first subset triaged) and "optimal" triaging thereafter.

The symbol—maximum STF—in front of the brackets reflects that the first subset of casualties to be treated or transported will also be optimized, thus making the entire ordering process optimal.

Linear Programming Formulation

The linear programming formulation maximizes the number of victims saved across all time periods, subject to constraints on the amount of medical resources available in each time period, and the number of victims with each severity score. Mathematically, if we let $V_{st}$=victims treated in time period t with severity score s, and $P_s$=the survival probability of treated victims with severity scores s, then the Linear Programming formulation is as follows:

$$\text{MAX } \Sigma_{st} P_s V_{st}$$

subject to $\Sigma_t V_{st}$=number of victims of score s, for all values of s
$\Sigma_s V_{st}$<=maximum number of victims that can be treated in time period t, for all values of s (this limits the resources).

The linear programming formulation identifies the number of victims with each score and in each time period to be treated such that the overall number of survivors is the maximum possible, given the limitation on available resources. The model of the present invention yields a completely feasible solution, solves very quickly using commercially available linear programming software, and does so even when operating under a large-scale mass casualty situation. The model of the present invention predicts survivability based on the survival probabilities used for each severity score, and is influenced by deteriorations-with-time rates as considered for the waiting victims. This formulation is easily expanded to directly include one or more of a variety of considerations, and/or to indirectly include the one or more variety of considerations through differentiated survival probabilities and/or differentiated deterioration-with-time rates. The variety of considerations could include, but would not be limited to, an availability of state-of-the-art, or lesser levels of treatment; a cause of or weapon used to create the casualty incident; type of trauma incurred by the casualty; a classification of the casualty, such as age or previous health condition; a type of care center appropriate for and available to the casualty, and/or treatment available at the incident scene; distances to the higher echelons of care; and facilities or equipment available for performance of the casualty management itself.

An Exemplary Embodiment of the Present Invention

By way of example, the following illustrates a possible casualty incident, and illustrates how the present invention would prioritize respective casualties for treatment in each time period to optimize total survivors over the entire event. The following embodiment has essentially equal results whether using dynamic or linear programming.

Assumptions:
  a) 2600 victims
  b) Of the 2600 victims, there are 200 victims in each RPM severity score category (RPM=0 through 12) (13 scores×200=2600)
  c) 500 victims can be treated in each period
  d) Victims will experience the following severity score deterioration-with-time for each time period:

| RPM value at beginning of time period | Score Point Decrease per time period |
|---|---|
| 8-12 | 1 |
| 5-7 | 2 |
| 3-4 | 3 |
| 2 | 2 |
| 1 | 1 |
| 0 | 0 |

Optimal Triage Protocol in accordance with dynamic or linear programming:

Time Period 1
Treat 200 with score of 5
Treat 200 with score of 6
Treat 100 with score of 7
Time Period 2
Treat 100 with original score of 7 (now score of 5)
Treat 200 with original score of 8 (now score of 7)
Treat 200 with original score of 9 (now score of 8)
Time Period 3
Treat 200 with original score of 10 (now score of 8)
Treat 200 with original score of 11 (now score of 9)
Treat 100 with original score of 12 (now score of 10)
Time Period 4
Treat 100 with original score of 12 (now score of 9)
Treat any victims still surviving (now score of 0)

Treatment or transportation continues through added time periods until all victims are triaged. The present invention is expected to save 1362 of the 2600 casualties when operating within the assumptions presented above.

Presented below is a continuation of the exemplary embodiment (i.e., 2600 victims, including 200 in each RPM category), illustrating how resource constraints impact survivor results and impact an order of treatment that maximizes survivor results. A comparison of survivor results is also presented between the methodology of the present invention and the worst-first sorting philosophy of START. For instance, in column 2, where 50 victims can be treated in each time period, the methodology of the present invention directs that casualties with an RPM score of 11 are treated in each of the first 4 time periods (50 per period), thereby first accounting for all casualties with an RPM score of 11; then casualties with an RPM score of 12 are treated in each of the next 4 time periods (50 per period), with continued treatment through added time periods as survivors permit. The scenario detailed above, where 500 victims can be treated in each time period, is also shown in table form, below, in column 5.

| Victims in Each RPM Category | | | | |
|---|---|---|---|---|
| 200 | 200 | 200 | 200 | 200 |
| Resources in Each Time Period | | | | |
| 50 | 100 | 200 | 500 | 800 |
| Treatment Order (by RPM score per time period) | | | | |
| $1^{st}$ 11 | 9 | 7 | 5, 6, 7 | 4, 5, 6, 7 |
| $2^{nd}$ 11 | 10 | 8 | 7, 8, 9 | 8, 9, 10, 11 |
| $3^{rd}$ 11 | 10 | 9 | 10, 11, 12 | 12 |
| $4^{th}$ 11 | 11 | 10 | 12, 4, 3 | — |
| $5^{th}$ 12 | 11 | 11 | 2, 1, 0 | — |
| $6^{th}$ 12 | 12 | 12 | — | — |
| $7^{th}$ 12 | 12 | — | — | — |
| $8^{th}$ 12 | — | — | — | — |
| Max Saves 1582 | 1582 | 1582 | 1582 | 1582 |
| Present Invention Saves 434 | 693 | 1068 | 1362 | 1474 |
| Worst First 135 | 135 | 135 | 720 | 1224 |

Comparison of START and the Present Invention

Recall that START employs severity categorizing based on three observations: respiration, perfusion, and mental status. In START, severity categorization is not specifically delineated, nor is it a computed score. Rather, START provides a method for quickly classifying a victim into one of four categories. Again, the categories are Ambulatory (or Minor), Immediate, Expectant (or Dead), and Delayed.

Ambulatory: All casualties are asked to stand up and walk to a specific area. All that can are designated as ambulatory or minor.

Immediate: A casualty is designated Immediate if breathing with a respiratory rate greater than 30 breaths/minute; OR, pulse is absent for 5 to 10 seconds or is "irregular"; OR, the victim cannot follow the commands "open your eyes", "close your eyes", or "squeeze my hand".

Expectant: A casualty is not breathing and does not start to breath with simple airway maneuvers.

Delayed: Any victim who does not fit into any of the three other categories

START employs the following treatment and/or transportation prioritization strategy: treat all immediates first, then delayeds, then others as opportunity provides. START does not distinguish among the Immediates, or among the Delayeds, with respect to prioritization for transport and upper echelon treatment. Prioritization for treatment and/or transportation is arbitrary among the Immediates, and then among the Delayeds. This can and does result in substantially more deaths than necessary, as demonstrated herein by example:

Immediates, in accordance with START doctrine, can take on the following present invention RPM component values: coded RR values of 2, 3, and 0; PR coded values of 1, 2, 3, and 4; and BMR values of 0, 1, 2, and 3. Accordingly, START Immediates can take on present invention RPM values between 1 through 10.

Delayeds, in accordance with START doctrine, can take on the following present invention RPM component values; coded RR values of 1, 3, and 4; coded PR values of 1, 2, 3, and 4; and a coded BMR value of 4. Accordingly, START Delayeds can take on present invention RPM values between 6 and 12.

As mentioned, START then makes no further effort to prioritize casualties categorized as Delayeds (other than the general categorization of being a Delayed) for treatment and/or transport, except to categorize them as an Immediate upon a qualifying reassessment.

The method of the present invention, however, distinguishes every casualty by specific severity score, and then rationally prioritizes each, based upon specific score, for treatment and/or transport. The method of the present invention can result in substantially more survivors than START, perhaps as many as seven times the number of survivors.

By way of example (this example is suggestive and not atypical): suppose there are 500 Immediates with present invention RPMs of 1 (survival probability=0.09 with state-of-art treatment); 500 Delayeds with present invention RPMs of 6 (survival probability=0.72 with state-of-art treatment); and 500 casualties can be treated at a time. As prescribed by doctrine, START triages the Immediates first (without taking into account survival probabilities or deterioration-with-time rates to determine priority), and experiences 45 survivors (0.090×500) among the 500 Immediates. START then experiences 205 survivors (0.410×500) one-half hour later upon triaging the 500 Delayeds (a survival probability of 0.410 is used because the 500 Delayeds have deteriorated to a present invention RPM of 4 in the one-half hour). Therefore, START saves 250 casualties.

The doctrine of the present invention directs the sending of the Delayeds first, experiencing 360 survivors (0.720×500), and experiencing (one-half hour later) an additional 26 survivors (0.052×500) from the Immediates, who began with RPM values of 1 and have deteriorated to a present invention RPM of 0. Therefore, the present invention saves 386 casualties.

A Variation of START as an Embodiment of the Present Invention

Based upon the less than optimal severity categorization of casualties in START, and the lack of ordering of treatment to maximize total survivors, the present invention also includes, in one aspect, a refinement of the START methodology to optimize total survivability. In this embodiment, incident victims are first categorized into one of the four START categories (Ambulatory, Immediate, Expectant, and Delayed) as described above, and by the START methodology described above.

Next, for those in the Immediate and Delayed categories, the respiratory, perfusion, and mental status observations are assessed for each victim in relation to an anatomic region of the body incurring injury, and survival probability rates are determined and assigned to each Immediate and Delayed casualty based upon the respiratory, perfusion, and mental status observations in relation to the anatomic region of the body incurring injury. The survival probability rates used can be assumed, can be data-based, or can be specifically compiled from existing trauma data-bases.

Then, each Immediate and Delayed casualty is further partitioned into one or more subcategories based upon the survival probability rate determined and assigned, so that victims grouped together (in the subcategories) have a lesser variation in likelihood of survival. The refinement of the Immediate and Delayed START categories, into subcategories, provides a more precise indicator of casualty severity for each Immediate and Delayed casualty, leading to a determination of an order of treatment providing maximum survivability. From this point, any of the methods of the present invention described above to determine an order of treatment can be employed to prioritize each of the subcategories of Immediate and Delayed casualties. The result is a more effective START triage method, employing several aspects of the present invention, directed to maximizing the number of survivors of a casualty incident.

An Instructional Program Directed to the Present Invention

In another aspect of the present invention, a training method and program is directed to training first responders in the triage methods of the present invention. First responders are defined generally as any participant in a triage operation, or any emergency care personnel involved in a casualty incident. The training methods and program could include case studies providing trainees with a variety of simulated triage experiences, each providing pre-determined trauma scenarios and injury data, such as casualty severity scores and resource availability, to challenge trainees to make triage decisions at the "incident scene", including determinations directed to an order of treatment and/or transportation for each of the incident casualties. For each triage decision made, the trainees could receive scored results based upon their decisions. The results could be in the form of a likely number of survivors resulting from the respective triage decisions.

Trainees (first responders) can initially use their past training and best judgment to direct their decision-making, then the training program could provide hints, leading questions, and/or additional information (i.e., general assistance) to guide and accelerate the learning process. The general assistance efficiently focuses the trainees on important features and method steps of the present invention, by helping the trainees discover flaws in their pre-training approach. The training process of the present invention can provide a dramatic learning experience, as trainees will experience an outcome based on their simulated triage decisions in terms of a number of survivors. Not only will the trainees learn the triage methods of the present invention, but they will fully understand and appreciate its benefits. Repetitive simulated training employing various case studies will hone skills, resulting in trainees experienced in the mechanics of the triage protocols of the present invention, confident in the outcome of the protocols, and prepared to use them correctly in a crisis. Reference materials could be provided, and case studies could be presented through video and animation, and offered, if desired, online.

Further Variations, Development, and Realizations of the Present Invention

As discussed, the present invention can determine survival probabilities based on physiologic scoring of each casualty at the scene, but the chaos of the incident scene dictates that the severity score be practical, meaning that its implementation is quick and straightforward. For at least blunt-injured and penetrating-injured casualties, RPM has proven it can meet these needs. RPM incorporates Respiratory Rate (RR), Pulse Rate (PR), and Best Motor Response (BMR), and has the following attributes:

- analyses indicate that RPM is a good predictor of survival probability
- the transition for emergency responders from START to RPM of the present invention is easily facilitated since it is based on the three assessments currently used (although not scored) in START.
- the method has been successfully tested with Navy Corpsmen and Navy Seals
- the RPM score can be computed in 45 seconds or less, for each casualty A triage tag, similar to existing triage tags, provides a simple mechanism to score and record the RPM values without requiring computations by emergency responders or hospital triage personnel.

Further Correlation of RPM to Survival Probability Estimates

The table below includes logistic function-generated survival probability estimates based on incident scene determined RPM values for 76,460 blunt-injured patients from a Pennsylvania Trauma Outcome Study. Note that this table provides survival probability estimates alternative to those provided previously, the probabilities of the table below being directed specifically to blunt injuries. Similar specific correlations can be developed for other types of trauma, and to age groupings of the victims.

| Scene RPM Value | Survival Probability Estimate for Blunt Injuries |
| --- | --- |
| 12 | .981 |
| 11 | .967 |
| 10 | .943 |
| 9 | .904 |
| 8 | .842 |
| 7 | .750 |
| 6 | .629 |
| 5 | .489 |
| 4 | .351 |
| 3 | .234 |
| 2 | .147 |
| 1 | .089 |
| 0 | .052 |

Notes Regarding START Classifications in Relation to RPM Values

START does not differentiate victim severity within categories, and severities within each category are widely disparate. This is because some casualties qualify for Immediate based on a single measure (e.g. respiratory rate) and others qualify based on two or three measures. Also, there is a large overlap in severity between Immediates and Delayeds.

This is a striking issue, not appreciated by START users. Indeed, as presented earlier, the RPM values for Immediates can vary from 1 to 10, and the RPM values for Delayeds can vary from 6 to 12. With respect to blunt-injury survival probability estimates based on RPM values, Immediates can vary from 0.089 to 0.943, and Delayeds can vary from 0.629 to 0.981. Accordingly, there is a significant (about 31 "point") overlap in survival probability (0.629 to 0.943), yet START protocol proposes triaging all Immediates before any Delayeds, as Immediates are deemed more critical.

If there is a desire by emergency providers to retain START categories, the present invention could rework START protocols so that, as an example, Immediates could be based upon RPM scores of 1-7, and Delayeds could be based upon RPM scores of 8-12. Or, for instance, an Orange category could be added, so that (Reds) Immediates could be based upon scores of 1-5, Oranges could be 6-8, and (Yellows) Delayeds could be based upon RPM scores of 9-12.

Rule-Based Triage as an Embodiment of the Present Invention

The present invention also includes Rule-Based Triage (RBT) methods, for use in triage scenarios having no access to computer processors, or where computer processing of transport and treatment order is inconvenient, or when communications between an incident scene and a remote computing location (i.e., when remote computing locations are employed) are disabled, unavailable, or inadequate. The goal of RBT is to provide practical, suboptimal triage by having available, prior to a casualty incident, an order of treatment or transport determined through triage simulation. By practical, we mean that RBT can be presented on a single sheet or card, or perhaps several cards, in graph, table, or spreadsheet form, for immediate use by triage officers upon arrival at an incident scene. By suboptimal, we mean that total survivability may approach, but may not achieve, the mathematical maximum.

Figure 3:
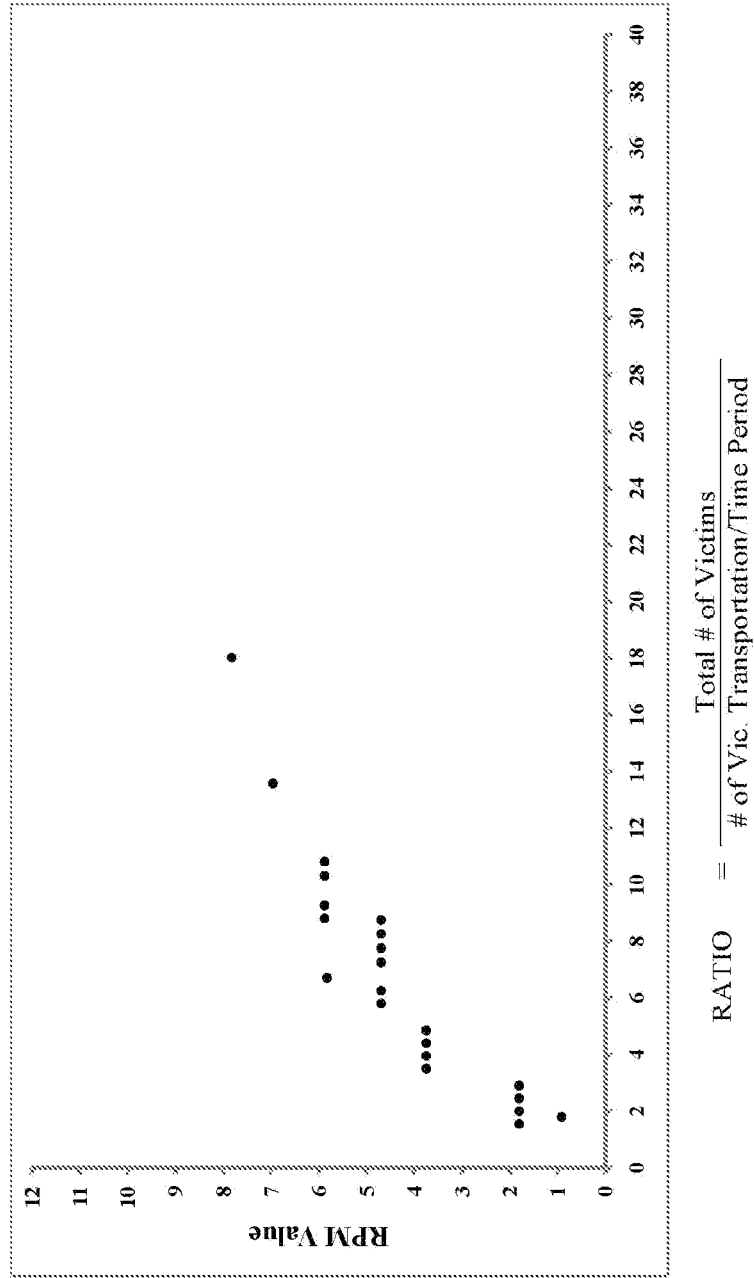
FIG. 3 is a graph illustrating rule-based triage determinations of treatment prioritizations, in accordance with another embodiment of the present invention.

One aspect of RBT is illustrated in FIG. 3, denoted RBT 1, which correlates R (the ratio of the total number of victims/number of victims that can be triaged per time period) to the smallest (lowest) RPM value (sRPMv) selected for triage in period 1. RBT 1 is implemented using a scattergram, with R plotted on the horizontal axis and sRPMv on the vertical axis.

RBT 1 was derived using triage methods of the present invention, determined by running many triage simulations of randomly generated (from various distributions) "victim state vectors" and variable resources (number of victims that can be treated over time period). A victim state vector requires a specification of 13 numbers which are the number of victims associated with each RPM value (from 0 to 12).

The many triage simulations, derived using the programming formulations described above, were gathered and analyzed to provide, in the form of FIG. 3, what a practical and efficient outcome would likely be, using the programming formulations of the present invention, without actually running the formulations at the time of the triage event. Development of RBT 1 can also exploit concepts such as data mining, pattern recognition, and/or other exploratory analyses. More specifically, the triage simulations used to create FIG. 3 assume a uniform distribution of RPM values across the victim population, meaning that every RPM value would be equally represented across all victims at the scene. Alternative representations of FIG. 3 could be prepared for selected non-uniform distributions, and/or specific incident and/or trauma types. Thus, a triage officer, at the incident scene, could quickly assess the scene, and choose the RBT 1 graph most closely representative of the incident, so that the resulting triage determinations using RBT 1 would be the most optimal of the practical results available.

Using the example casualty incident scene provided previously, and reiterated below, the following illustrates how RBT 1 of the present invention would prioritize respective casualties for treatment in each time period to provide practical and nearly optimal total survivability without use of computers at the incident scene, or without algorithmic calculation at the scene.

Assumptions:
a) 2600 victims
b) Of the 2600 victims, there are 200 victims in each RPM severity score category (RPM=0 through 12) (13 scores×200=2600)
c) 500 victims can be treated in each period
d) Victims will experience the following severity score deterioration-with-time for each time period:

In this example, R (the ratio of the total number of victims/number of victims that can be triaged per time period) would be 2600/500=5.2. R=5.2 would correlate, on FIG. 3, with a RPM score of 5. Accordingly, time period 1 (where 500 victims can be treated) would include treatment of 200 victims with a RPM score of 5 (i.e., all of the RPM=5 victims), 200 victims with a RPM score of 6 (i.e., all of the RPM=6 victims), and 100 victims with a RPM score of 7. Triage determinations in subsequent time periods would continue progressing through ever increasing RPM values as each RPM value is exhausted, at the rate of 500 victims per period.

Another aspect of RBT, denoted RBT 2, is illustrated in the table below, and is based on survival probability estimates using blunt-trauma data and deterioration-with-time estimates provided by trauma surgeons. Alternative RBT 2 tables could be developed using survival probability data specific to other types of trauma, and/or evidence based data directed to the deterioration-with-time of RPM score, considering deterioration-with-time generally, or in light of the specific trauma in question.

Using the survival probability data and the trauma surgeon estimates, RBT 2 employs greedy algorithm techniques to provide practical and suboptimal triage, for use where computers are not available (or convenient) to determine optimal programming formulations. Again, techniques other than greedy algorithms could be employed, techniques such as data mining, pattern recognition, and/or other exploratory analyses to formulate prioritization results without employing the computer processing of programming formulations described herein at the time of the triage incident. RBT 2 is distribution independent, meaning that the survivability results provided by the table are not dependent, from a standpoint of optimality, on whether a uniform distribution of the victims across all RPM values occurs.

In the RBT 2 table, below, each time period is listed, followed by a triage order based upon the original RPM score. The original RPM score refers to that score initially established at the incident scene. Again, rule-based triage does incorporate victim deterioration-with-time, but the re-evaluation of RPM score due to victim deterioration-with-time is not displayed in the table. Rather, the prioritizations listed for every time period, while considering victim deterioration-with-time, refer to the RPM score originally established.

Again using the example casualty incident scene provided above, a triage officer employing RBT 2 at the example incident scene, would triage, in time period 1 (where 500 victims can be treated), 200 victims with a RPM score of 6 (i.e., all of the RPM=6 victims), 200 victims with a RPM score of 5 (i.e., all of the RPM=5 victims), and 100 victims with a RPM score of 7 (thereby completing the 500 victims treated for this time period). Then, in time period 2 (again, where 500 victims can be treated), would triage 200 victims with a RPM score of 8 (i.e., all of the RPM=8 victims), 0 victims with an RPM=6 (as all RPM=6 victims have been treated in time period 1), 200 victims with a RPM score of 9 (i.e., all of the RPM=9 victims), 0 victims with an RPM=5 (as all RPM=5 victims have been treated in time period 1), and 100 victims with a RPM score of 4 (thereby completing the 500 victims treated for this time period).

| Time Period | RBT 2 RPM Triage Order | | | | | | | | | | | | |
|---|---|---|---|---|---|---|---|---|---|---|---|---|---|
| 1 | original RPM value | 6 | 5 | 7 | 4 | 8 | 3 | 9 | 2 | 1 | 10 | 11 | 12 | 0 |
| 2 | original RPM value | 8 | 6 | 9 | 5 | 4 | 3 | 12 | 7 | 10 | 11 | 2 | 1 | 0 |
| 3 | original RPM value | 7 | 8 | 9 | 5 | 4 | 10 | 11 | 6 | 12 | 3 | 2 | 1 | 0 |
| 4 | original RPM value | 6 | 5 | 11 | 12 | 7 | 8 | 9 | 10 | 4 | 3 | 2 | 1 | 0 |
| 5 | original RPM value | 9 | 10 | 6 | 7 | 8 | 11 | 12 | 5 | 4 | 3 | 2 | 1 | 0 |
| 6 | original RPM value | 7 | 8 | 11 | 6 | 9 | 10 | 12 | 5 | 4 | 3 | 2 | 1 | 0 |

Another aspect of RBT, denoted RBT 3, is illustrated in the RBT 3 table below, and provides another aspect of ordering of treatment for suboptimal triage where computers are unavailable, or use at the scene is inconvenient, and/or communications to an off-site processing center (if employed) are compromised, non-existent, or undesirable. RBT 3 does not break out the ordering by time period, but instead provides one order of treatment for all time periods based upon the estimated time necessary to completely clear (i.e., assess and transport) all casualties from the incident scene.

In providing one order of treatment for all time periods based upon the estimated time necessary to completely clear the incident scene of victims, RBT 3 provides three incident scene categories, Resources Stressed, Resources Taxed, Resources Overwhelmed, and provides an order of treatment for each. Resources Stressed refers to a multiple casualty incident requiring about one hour to completely clear the scene of victims; Resources Taxed refers to a scene requiring approximately 2 to 3 hours to clear of victims; and Resources Overwhelmed refers to a scene requiring greater than 3 hours to clear of victims. Alternative variations of RBT 3 could provide a greater or lesser number of categories, each category delineating a time range necessary to completely clear the incident scene of victims. The ordering illustrated in RBT 3 is directed to a composite of blunt and penetrating trauma. Alternative embodiments of RBT 3 can be specific to other trauma types, providing a more optimal ordering for an incident primarily involving, in whole or in part, that specific trauma type, or RBT 3 can illustrate a general ordering to address casualty incidents of any trauma type.

RBT 3
Resources Stressed:
  Triage Order: 6 5 4 3 2 7 1 0 8 9 10 11 12
Resources Taxed:
  Triage Order: 5 6 7 8 4 9 3 2 1 10 11 12
Resources Overwhelmed:
  Triage Order: 6 7 8 5 9 10 4 3 2 1 11 12

The ordering reflected in RBT 3, as that reflected in RBT 1 and RBT 2, can be determined by running triage simulations of random victim scenarios (i.e., a various number of victims with various injury types across a random or uniform range of casualty severity score) and resource constraints, the ordering of treatment or transport being determined prior to the respective incident so that a triage officer could implement an order of treatment or transport based upon a previous simulation, or by matching characteristics of various previous simulations to the respective incident scene to select the most adequate simulation result for use. Or, RBT 3 ordering determinations can exploit data mining, pattern recognition and/or greedy algorithms.

In this embodiment of RBT 3, the Resources Stressed portion was determined using a greedy algorithm, considering that there would be some victim staging to await transport to definitive care, and accordingly, experience some deterioration. The Resources Taxed and Resources Overwhelmed portions of RBT 3 rely on various triage simulations.

To determine the Resources Stressed portion of RBT 3 using the greedy algorithm, the following RPM scores, survival probabilities, and victim deterioration-with-time rates per 30 minutes were used. Considering the expected RPM value after one time period (30 minutes) of deterioration, as reflected in column 3, a change in survival probability is determined, as reflected in column 4. For example, a victim having an original RPM value of 7 would deteriorate to a 6 after one time period; the change in survival probability would therefore be 0.09 (0.83−0.72=0.09). The greedy method then orders victims to minimize the impact of deterioration, by ranking victims by RPM score in decreasing order relative to the expected change in survival probability.

As reflected in the table, the greedy algorithm reflects the following order: 6 5 4 3 2 7 1 0 8 9 10 11 12

| Original RPM | Original Survival Propability | Expected RPM After 30 Minutes | Change in Survival Probability | Ranked by Largest Change in RPM |
|---|---|---|---|---|
| 12 | .992 | 12 | 0 | 8 |
| 11 | .985 | 11 | 0 | 8 |
| 10 | .97 | 10 | 0 | 8 |
| 9 | .94 | 9 | 0 | 8 |
| 8 | .90 | 8 | 0 | 8 |
| 7 | .83 | 6 | .09 | 6 |
| 6 | .72 | 4 | .31 | 1 |
| 5 | .57 | 3 | .30 | 2 |
| 4 | .41 | 2 | .25 | 3 |
| 3 | .27 | 1 | .18 | 4 |
| 2 | .16 | 0 | .11 | 5 |
| 1 | .09 | 0 | .038 | 7 |
| 0 | .052 | 0 | 0 | 8 |

*The RPM scores of 0, 8, 9, 10, 11 and 12 were tied with zero expected change in survival probability, and were ordered by increasing RPM values.

Transportation Mode Determination as an Embodiment of the Present Invention

In another aspect of the present invention, transportation mode determination (e.g., whether Medevac eligible and what type of transportation to use), determination of whether to transport to a trauma center, and/or determination/selection of a specific trauma center/care facility for treatment, in non-mass casualty triage is performed.

Non-mass casualty triage generally refers to a situation where resources are immediately available for all casualties of an incident. Non-mass casualty triage could involve multiple casualties, or just one casualty. In either event, transportation modes are immediately available, and all required levels of trauma treatment are immediately available, to adequately and fully triage all casualties of the incident. In non-mass casualty triage, determinations are directed to efficiency, where the casualty incident provides enough time (more than in mass casualty triage) for a thorough casualty assessment. As articulated above, recall that mass casualty triage generally refers to an incident where the number of casualties exceeds or taxes available resources, where resource access is restricted or limited, or where resources have to be staged, and triage protocols are required to effectively allocate the limited resources.

In non-mass casualty triage, transportation mode determination (eligibility) or selection, the determination of whether to transport a casualty to a trauma center, and/or the determination/selection of a specific trauma center/care center, can involve use of STM RPM severity scoring by age categories/adjustments (i.e., age adjustment RPM scores), by type of trauma, together with anatomic and mechanism of injury (MOI) considerations in non-mass casualty events, to identify trauma patients whose expected survivorship might increase due to the time savings associated with Medevac transport to a trauma center/care facility, and to significantly improve triage efficiency using evidence-based methods, causal factor analysis, regression, and search theory to significantly improve triage efficiency. Medevac transport generally refers to medically equipped vehicles, whether ground (e.g., ambulances) or aircraft (e.g., air ambulances—whether helicopter or fixed wing aircraft). In certain aspects of the invention, determination of Medevac eligibility refers specifically to whether air transport is a necessary and efficient mode of transport to the trauma center/care facility. In other aspects, Medevac eligibility refers to whether a medically equipped vehicle is necessary and efficient, whether by ground or air.

Transportation mode determination, as an aspect of the present invention, understands that more time allows for a more thorough patient assessment in non-mass casualty events, that patient survival probability can be greatly influenced by specific injuries, ages, mechanism of injury (MOI), and type of trauma; and that, by using evidence, search theory, causal factor analysis, regression, and the method steps and mathematical or analytical programming techniques detailed above (such as, but not limited to dynamic or linear programming formulations—score based mathematical algorithms), overtriage can be significantly reduced while maintaining target levels of undertriage. More specifically, the current costly standard of accepting 25-50% overtriage, as a target level, is not necessary to achieve the 0-5% undertriage target level, as cited in the Center for Disease Control (CDC) publication, "Field Triage Decision Scheme: The National Trauma Triage Protocol;" MMWR, Jan. 23, 2009, Vol. 58/RR-1, p. 10.

In one embodiment of transportation mode determination of the present invention, the transportation mode determination/selection in non-mass casualty triage can be determined by identifying patients as candidates for the fastest mode of transportation (to trauma center), whether by air or ground, as defined by the expected increase in time-dependent survival probability based on the physiologic, anatomic, mechanism of injury and type of trauma of the patient, and on the proximal location of the patient to transport and treatment resources, including the capabilities of these resources. Specifically, this embodiment determines transportation mode based on a patient's expected survival probability as compared to a desired, pre-selected level of undertriage, where the patient's expected survival probability is assessed from a hierarchical comparison of the patient's condition to 1) RPM severity scoring and age categories/adjustments; 2) type of trauma; 3) anatomic injuries; 4) mechanism of injury (MOI); 5) victim en route deterioration with time rate for each mode of transport considered; 6) transfer time by mode to the trauma center; which could include weather dependent and mode specific travel time estimates; and 7) computation of the expected survival probability by mode. The present invention provides that EMS practitioners can choose a far more precise (or any) level of undertriage risk. In any case, methodology results instruct that EMTs can eliminate a significant number of Medevac flights (air transport), while maintaining an adequate level of care. As an example, based upon current evidence, a selection of up to a 5% undertriage risk would mean eliminating 62% or more of eligible Medevac flights; a selection of up to 2% undertriage risk would mean eliminating up to 46% of eligible flights (excluding patients that were flown and not admitted).

In another aspect of the invention, and in view of the statistics above, additionally considered is the American College of Surgeons criteria for sending a patient to a trauma center in non-mass casualty incidents, and identification of the physiologic, anatomic, mechanism of injury, and type of trauma characteristics that impact survival probability. This criteria can be factored with one or more of the RPM scores, the patient's age, and travel time information to determine the patient's transport mode (i.e., the transportation mode necessary for survival and/or for best or maximum efficiency of resources), whether to transport, and/or to select which care facility in which to transport.

Figure 4:
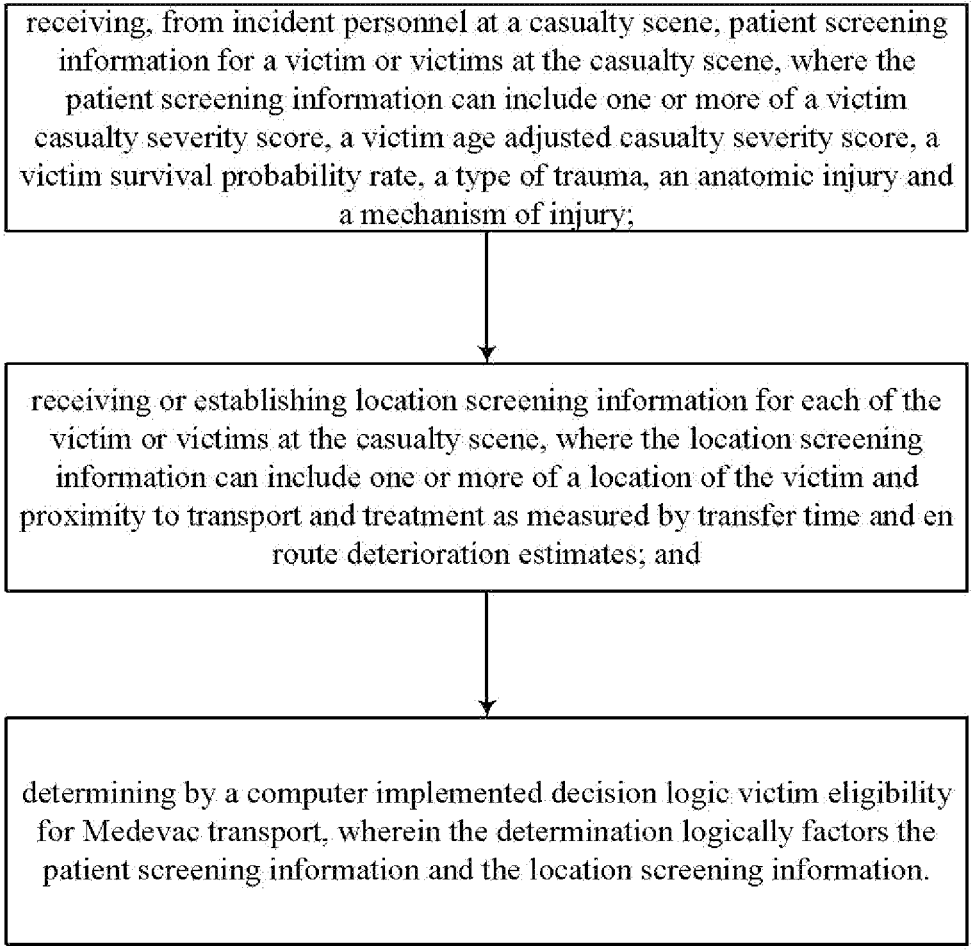
FIG. 4 is a flow diagram illustrating a method of transportation mode determination in accordance with one embodiment of the present invention.

In a high level aspect of the invention, as illustrated in FIG. 4, a method of transportation mode determination in non-mass casualty triage is provided and involves receiving, from incident personnel at a casualty scene, patient screening information for a victim or victims at a casualty scene. Additionally, location screening information for the victim or victims at the casualty scene is established and received. The patient screening information and location screening information can be input into a computer. Then, victim eligibility for Medevac transport is determined by logically factoring the patient screening information and the location screening information. The determination can be performed by computer implemented decision logic, and the determination can be directed to eligibility for air ambulance transport, or eligibility for transport by any medically equipped vehicle (whether air or ground).

As noted in FIG. 4, the patient screening information can include, but is not limited to, one or more of a victim casualty severity score, a victim age adjusted casualty severity score, a victim survival probability rate, a type of trauma, an anatomic injury and a mechanism of injury. The location screening information can include, but is not limited to, one or more of a location of the victim, a proximity of the victim to Medevac transport mode options, proximity of the victim to a treatment facility as measured by transfer time required by transport mode options, and relative to en route deterioration estimates.

In other aspects, Medevac dispatch can be based on a series of screening criteria. If a patient has an RPM below a certain level, is of a certain age, and/or has one of a number of specific injuries, the patient would be eligible for Medevac transport (e.g. whether by air or ground). Of those patients determined eligible, the actual transport mode selected (or determined) would be based on a time comparison between ground and air that reflects the location of the emergency scene, the location of the transport unit, the expected en route deterioration, the weather, and the traffic, based on the total necessary transfer time required to move the patient to a designated trauma center or care facility.

In one embodiment, patients deemed ineligible for Medevac (e.g., ineligible for airlift) transport have an expected survival probability above a certain threshold (e.g. 95%), and will have little or no expected deterioration within some specified time frame (e.g. 90 minutes). The specified time frame could coincide with the maximum amount of time before a patient would begin deterioration.

Figure 5:
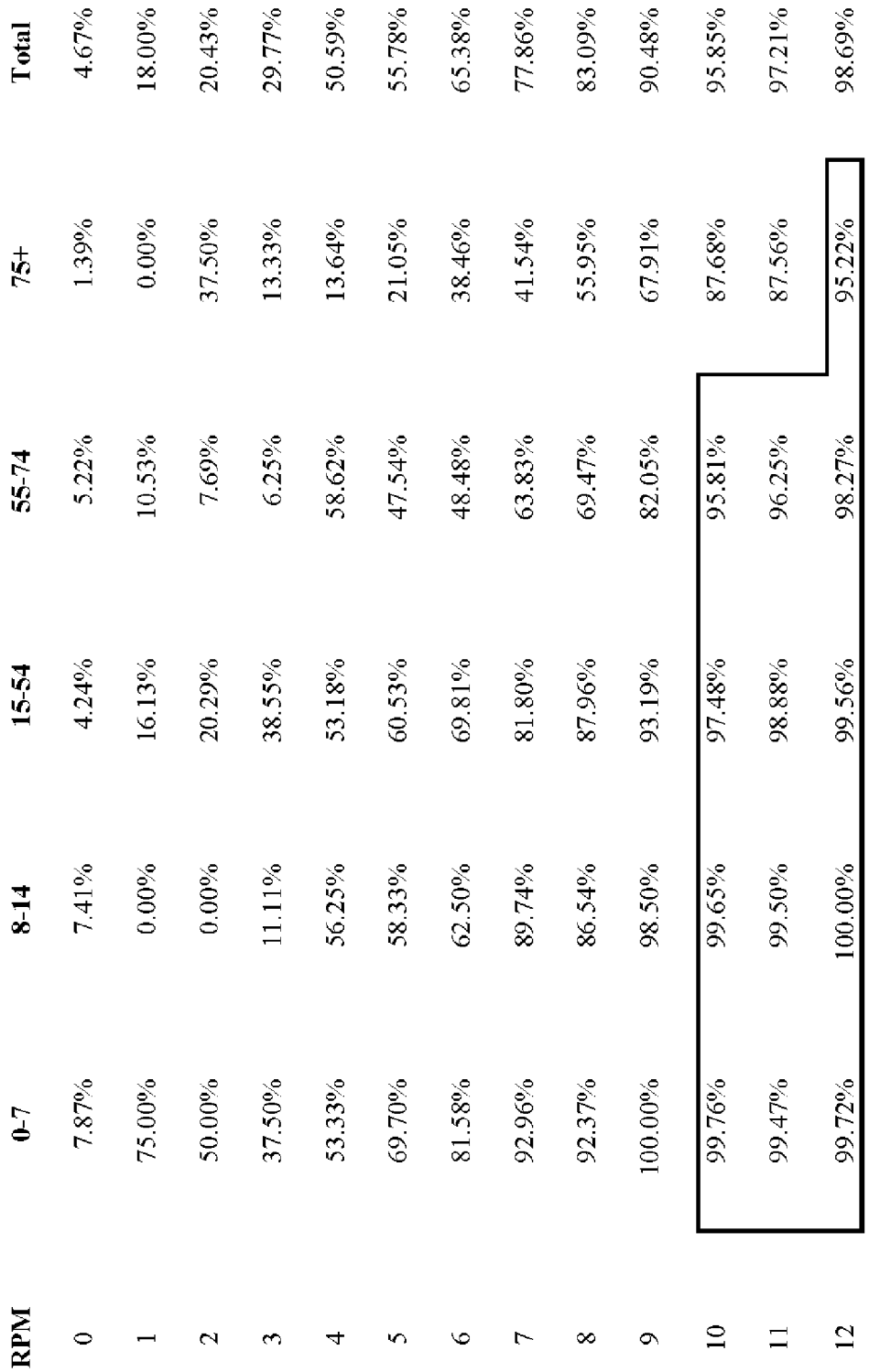
FIG. 5 is a chart illustrating STM RPM severity score relative to victim age groups, where patients deemed ineligible for Medevac transport have an expected survival probability above 95%, in accordance with one embodiment of the present invention.
Figure 6:
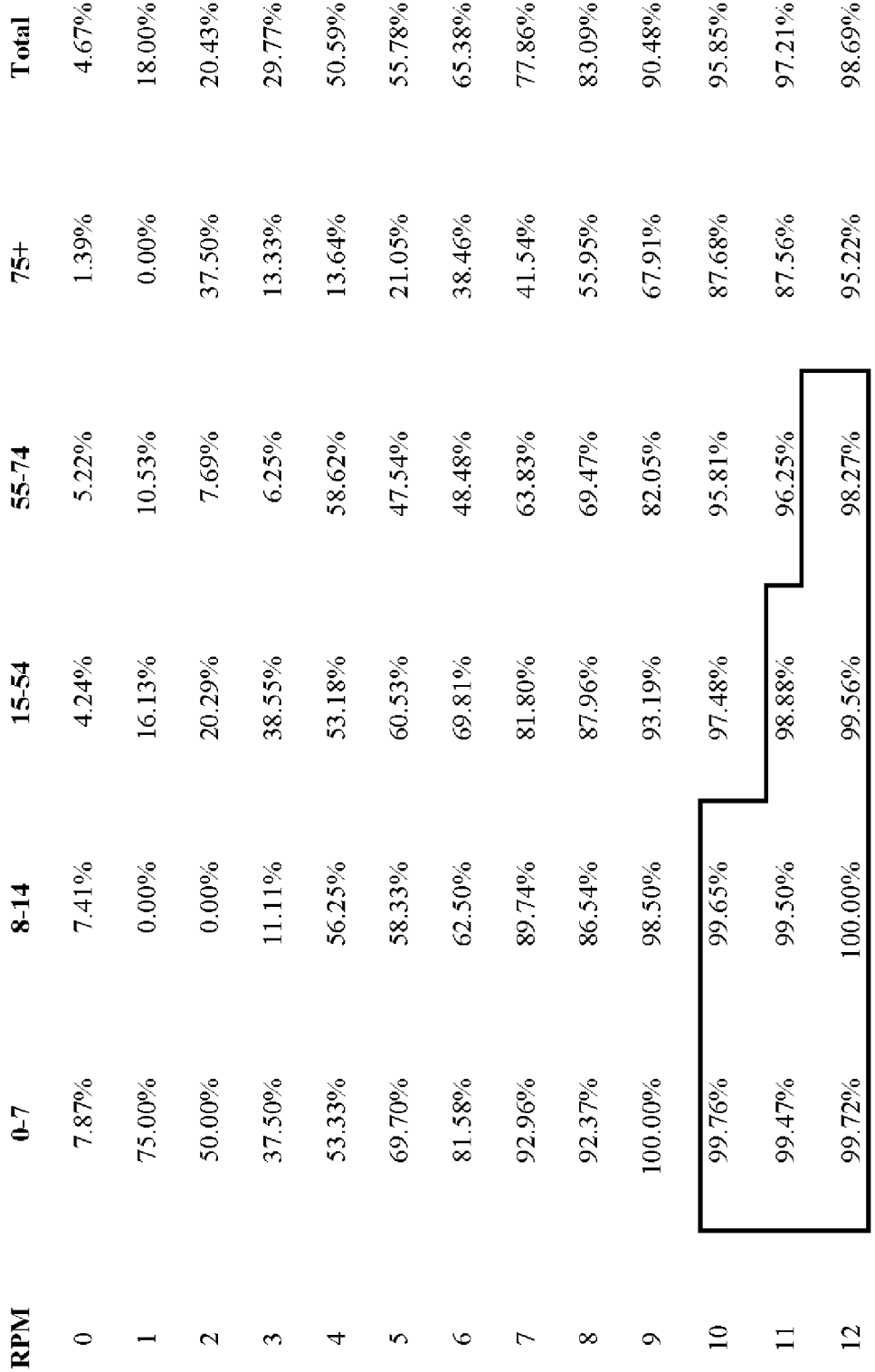
FIG. 6 is a chart illustrating STM RPM severity score relative to victim age groups, where patients deemed ineligible for Medevac transport have an expected survival probability above 98%, in accordance with one embodiment of the present invention.

Exemplary resulting embodiments are shown in FIGS. 5 and 6. FIG. 5 illustrates a correlation of STM RPM severity score relative to victim age groups, where patients deemed ineligible for Medevac transport (here, specifically directed to air transport—Medevac flights) have an expected survival probability above 95%, where survival probability is determined by considering type of injury, mechanism of injury and victim physiological screens. FIG. 6 is a similar correlation, where 98% survival probability is used as the threshold for ineligibility for air transport.

Figure 7:
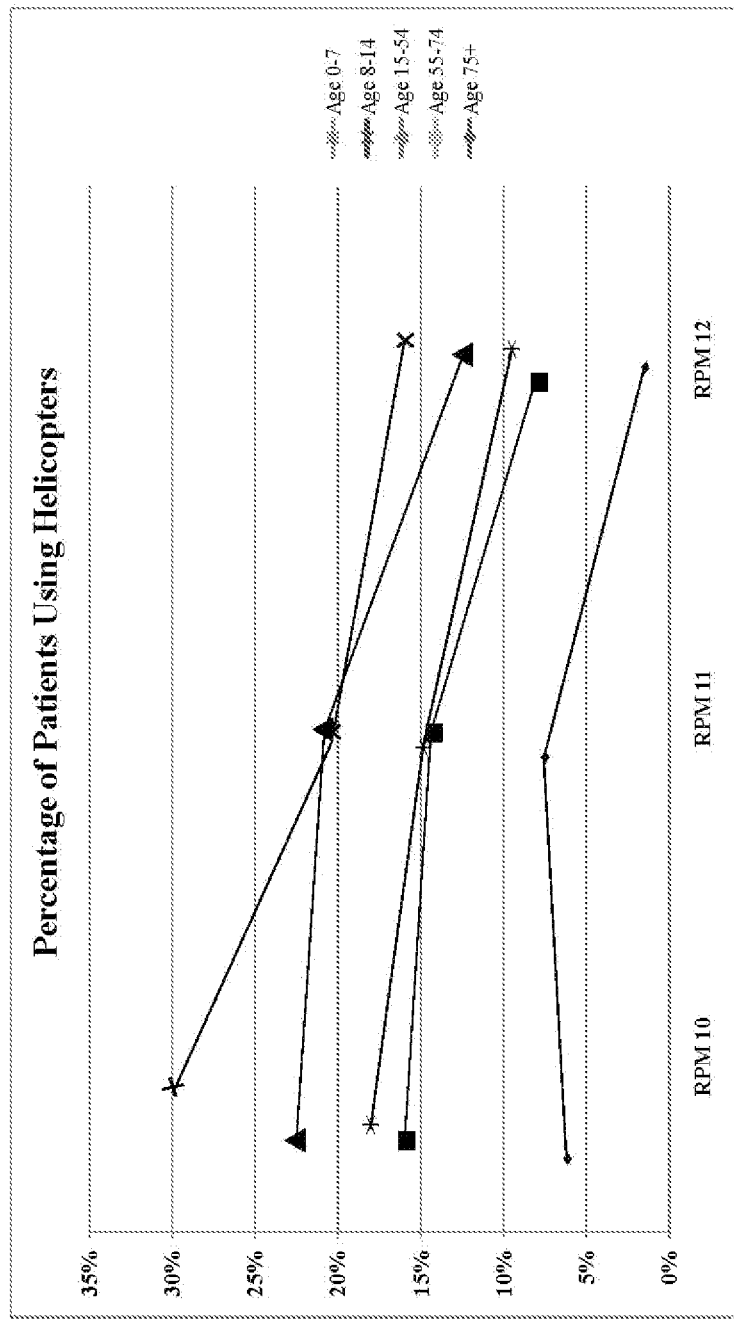
FIG. 7 is graph illustrating the current percentage of victims receiving Medevac airlift transport by age group, relative to STM RPM severity score, and evidencing advantages of the methods and system of the present invention.

Accordingly, methods of the present invention have resulted in the elimination of more than 50% of Medevac flights, while having no impact on mortality of state of heatlh. FIG. 7 illustrates this point, showing the current percentage of victims receiving Medevac flights by age group, relative to STM RPM severity score. A comparison of FIG. 7 to FIGS. 5 and 6 evidences the extent of overtriage of our youth, and possible undertriage of the elderly (as directed to Medevac flights). More specifically, a comparison of the figures evidences that elderly patients are much less likely to be air transported, yet their survival probabilities for respective STM RPM scores are much lower than that for younger adults and children; therefore, the elderly should receive Medevac flights much more often, rather than much less. In view of the foregoing, the present invention provides a method and system providing countless savings to medical resources, without impacting victim survivability or victim state of health. Additionally, present invention also provides for a reduction in mortality, along with a reduction in overtriage.

Further, the methods and system of the present invention evidences, addresses and solves a recent concern of the Center for Disease Control (CDC), in their publication, "Field Triage Decision Scheme: The National Trauma Triage Protocol;" MMWR, Jan. 23, 2009, Vol. 58/RR-1, p. 25. At page 25, it is reported that evaluation of more than 2300 studies found that "available evidence was insufficient to support any standards regarding triage of geriatric trauma patients." The present invention not only identifies inadequacies in triage of the elderly, but also provides a method to rectify the problem.

Examples of Transportation Mode Determination

Version 1

In one embodiment of the present invention:

A paramedic or Emergency Medical Technician (EMT) would relay information on a patient's condition into the STM Medevac dispatch methodology (i.e., the method and system of the present invention) directly or through an EMS dispatch operator. Where local protocols or law requires consultation with a physician, patient condition information would be further relayed to a physician, whether directly or via Medevac or EMS dispatch. If required, necessary approvals would be incorporated into this methodology. The methodology determines a patient's eligibility for Medevac transport. Eligibility is based on a patients expected survival probability and rate of deterioration as determined by a series of criteria including age dependent physiological, anatomic, mechanism of injury (MOI), type of trauma, and ground transport time parameters.

The physiological screen uses the age-based Sacco Score (RPM score). If a patient's age/score combination meets designated criteria, that patient is deemed Medevac eligibile. If the patient does not meet the physiological criteria, anatomic injuries, mechanism of injury and type of trauma (all of the above referred to as patient screening information) are assessed in hierarchical order based on their expected impact as determined through search theory analysis. If a patient has any of the specified injuries or conditions, the patient is Medevac eligible. Transport mode choice for eligible patients is based on the location of the patient and their proximity to transport and treatment, as measured by the transfer time (i.e. dispatch time, vehicle prep time, to-scene travel time, on-site time including patient loading, to-ED travel time, and patient unload time) required by each mode to move the patient to definitive care, in consideration of the patient's expected en route deterioration (all of the above referred to as location screening information). The location screens could be applied prior to patient condition screens.

Version 2

In another embodiment of the present invention:

A paramedic or Emergency Medical Technician (EMT) would relay information on a patient's condition into the STM Medevac dispatch methodology directly or through an EMS dispatch operator. The methodology determines a patient's eligibility for transport. Eligibility is based on a patients expected survival probability and rate of deterioration as determined by a series of age dependent physiological, anatomic, mechanism of injury, type of trauma, screens and ground transport time parameter bounds. The physiological screen can use the age-based Sacco Score (RPM score). Transport mode selection for Medevac eligible patients is based on the transfer time (i.e. dispatch time, vehicle preparation time, to-scene travel time, on-site time including patient loading, to-ED travel time, patient unload time) of each mode.

In one aspect:

If a patient's age/score combination meets designated criteria, that patient is deemed Medevac eligibile. If the transfer time for the air transport is faster than ground transport, then a Medevac unit would be dispatched and the patient transported by helicopter to the designated treatment facility.

In another aspect:

If a patient's age/score combination does not meet the designated criteria, but the patient has one or more of a number of specific injuries or conditions, that patient is deemed Medevac eligibile. If the transfer time for air transport is faster than that of ground transport, then a Medevac unit would be dispatched and the patient transported by helicopter to the designated treatment facility.

In still another aspect:

If a patient is deemed Medevac eligible, either by the age/score combination or by injury or condition, but the transfer time is greater for air than ground transport, the patient would be transported by ground unit to definitive care.

Data Trends and Insights into Transportation Mode Determination of the Present Invention The table below summarizes a review of just over 100,000 trauma patients. It shows survival percentages by mode, and by patient acuity as represented by the scores. There seems to be no advantage in using helicopters in mortality for patients with high survival probabilities (i.e., those with higher scores). An examination of the number of patients who died within the first hour (data not included here) indicates a life savings advantage below a score of 8 for helicopters, and an advantage for ambulances otherwise. Few patients that die with normal physiology (i.e., scores of 12), die within the first hour.

| Comparison Lives and Dies by Mode and RPM Value | | |
|---|---|---|
| Sacco Score | Ambulance % live | Helicopter % live |
| 0 | 3% | 4% |
| 1 | 10% | 12% |
| 2 | 17% | 31% |
| 3 | 29% | 35% |
| 4 | 40% | 58% |
| 5 | 52% | 49% |
| 6 | 63% | 66% |
| 7 | 74% | 72% |
| 8 | 80% | 75% |
| 9 | 89% | 89% |
| 10 | 95% | 94% |
| 11 | 96% | 96% |
| 12 | 98% | 98% |

Extension of STM to Medevac Dispatching

By computing a patient's RPM score, estimating their age, knowing the dominant type of trauma suffered (i.e. blunt, penetrating and blast overpressure-like), the patient's specific injuries, the mechanism of injury, and knowing the patient's location relative to the trauma center, relative to local ED, and relative to the nearest available means of transport, present invention methodology can estimate survival probability by mode and destination location. Travel time must be explicitly considered, and other factors such as mechanism of injury, to determine impact on mortality, both dependently and independently of physiology.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention.

What is claimed:

1. A method of transportation mode determination in non-mass casualty triage, the method comprising the steps of:
receiving, from incident personnel at a casualty scene, a casualty severity score for a victim at a casualty scene;
assigning, or separately establishing, a survival probability for the casualty severity score based upon at least one characteristic of the respective victim or of an incident responsible for the victim;
assigning, or separately establishing, a casualty severity score deterioration-with-time rate based upon at least one characteristic of an availability of state-of-the art, or lesser levels of treatment; a type of anatomic injury incurred by the victim; an age of the victim; a mechanism of injury; treatment available at the casualty scene; treatment available at other facilities; distances to the other facilities; and facilities or equipment available for performance of care;
inputting at least the survival probability and the casualty severity score deterioration-with-time rate into a computer; and
determining by a computer implemented decision logic victim eligibility for Medevac transport, wherein the determination logically factors the survival probability and the casualty severity score deterioration-with-time rate.

2. The method of claim 1, wherein, if the victim is determined eligible for Medevac transport, further determining a mode of Medevac transport, wherein the determination logically factors one or more of a location of the victim, proximity of the victim to transport mode options, proximity of the victim to the treatment facility as measured by transfer time required by transport mode options relative to the severity score deterioration-with-time rate.

3. The method of claim 1, wherein, if the victim is determined ineligible for Medevac transport, further determining whether the victim is eligible for care at a trauma center or care facility, wherein the determination logically factors one or more of a type of injury incurred by the victim; an age of the victim; an age of adjusted RPM score; treatment available at the casualty scene; treatment available at other facilities; physiologic characteristics of the victim and mechanism of injury.

4. The method of claim 1, wherein a plurality of victims exist at the casualty scene, and wherein victim eligibility for Medevac transport is determined by a computer implemented decision logic for each of the plurality of victims by logically factoring the survival probability and the casualty severity score deterioration-with-time rate for each victim.

5. The method of claim 4, wherein, for all victims determined eligible for Medevac transport, further determining an order of treatment, or transport for treatment, for all victims determined eligible for Medevac transport, the method further comprising the steps of:
receiving information indicative of triage resources available for the plurality of victims;
inputting the information indicative of the triage resources available into a computer; and
determining by a computer implemented decision logic an order of treatment, or transport for treatment, for each of the plurality of victims determined eligible for Medevac transport, wherein the decision logic mathematically factors the casualty severity score for each victim and the triage resources available for the plurality of victims.

6. The method of claim 4, further determining an order of treatment for the plurality of victims, the method further comprising steps of:
receiving information indicative of triage resources available for the plurality of victims;
inputting the information indicative of the triage resources available into a computer; and
determining by a computer implemented decision logic an order of treatment for the plurality of victims, wherein the decision logic mathematically factors the casualty severity score for each victim and the triage resources available for the plurality of victims.

7. A method of transportation mode determination in non-mass casualty triage, the method comprising the steps of:
receiving from incident personnel at a casualty scene, or separately establishing, patient screening information for a victim at a casualty scene, wherein the patient screening information includes or factors a casualty severity score of the victim, a survival probability for the victim based upon the casualty severity score, and a casualty severity score deterioration-with-time rate;
inputting, as necessary, the patient screening information for the victim into a computer;
receiving location screening information for the victim at the casualty scene;
inputting the location screening information for the victim into a computer; and
determining by a computer implemented decision logic victim eligibility for the Medevac transport, wherein the determination logically factors the patient screening information and the location screening information.

8. The method of claim 7, wherein the patient screening information further includes or factors one or more of a victim age adjusted casualty severity score, a type of trauma, an anatomic injury and a mechanism of injury.

9. The method of claim 7, wherein the location screening information includes one or more of a location of the victim and proximity to transport and treatment as measured by transfer time and en route deterioration estimates.

10. The method of claim 7, wherein, if the victim is determined eligible for Medevac transport, further determining a mode of Medevac transport, wherein the determination logically factors the patient screening information and the location screening information.

11. The method of claim 10, wherein the location screening information includes one or more of a location of the victim, a proximity of the victim of Medevac transport mode options, proximity of the victim to a treatment facility as measured by transfer time required by transport mode options relative to the severity score deterioration-with-time rate.

12. The method of claim 7, wherein, if the victim is determined ineligible for Medevac transport, further determining whether the victim is eligible for care at a trauma center or care facility, wherein the determination logically factors one or more of a type of injury incurred by the victim, an age of the victim; an age adjusted RPM score; treatment available at the casualty scene, treatment available at other facilities, physiologic characteristics of the victim and mechanism of injury.

13. The method of claim 7, wherein a plurality of victims exist at the casualty scene, and wherein victim eligibility for Medevac transport is determined by a computer implemented decision logic for each of the plurality of victims.

14. The method of claim 13, wherein, for all victims determined eligible for Medevac transport, further determining an order of treatment, or transport for treatment, for all victims determined eligible for Medevac transport, the method further comprising the steps of:
receiving information indicative of triage resources available for the plurality of victims;
inputting the information indicative of the triage resources available into a computer; and
determining by a computer implemented decision logic an order of treatment, or transport for treatment, for each of the plurality of victims determined eligible for Medevac transport, wherein the decision logic mathematically factors the patient screening information, the location screening information and the triage resources available for the plurality of victims.

15. The method of claim 13, further determining an order of treatment for the plurality of victims, the method further comprising steps of:
receiving information indicative of triage resources available for the plurality of victims;
inputting the information indicative of the triage resources available into a computer; and
determining by a computer implemented decision logic an order of treatment for the plurality of victims, wherein the decision logic mathematically factors the patient screening information, the location screening information and the triage resources available for the plurality of victims.

16. The method of claim 7, wherein eligibility for Medevac transport refers to eligibility for a Medevac flight.

17. The method of claim 7, wherein eligibility for Medevac transport refers to eligibility for transport by any medically equipped vehicle (air or ground).

18. A method of transportation mode determination in non-mass casualty triage, the method comprising the steps of:
receiving, from incident personnel at a casualty scene, one or more physiological characteristics of a victim at the casualty scene;
receiving from the incident personnel, or separately establishing, a casualty severity score for the victim based upon the physiological characteristics of the victim;
assigning, or separately establishing, a survival probability for the victim from the casualty severity score;
assigning, or separately establishing, a casualty severity score deterioration-with-time rate based upon one or more of the physiological characteristics of the victim, a type of anatomic injury incurred by the victim; an age of the victim; a mechanism of injury; a type of trauma, and ground transport time parameters;
inputting at least the survival probability and the casualty severity score deterioration-with-time rate into a computer; and
determining by a computer implemented decision logic victim eligibility for Medevac transport, wherein the determination logically factors the survival probability and the casualty severity score deterioration-with-time rate.

19. The method of claim 18, wherein the survival probability is assessed from consideration of one or more of casualty severity score, casualty severity score with age adjustment type of trauma, anatomic injury, mechanism of injury, victim en route deterioration with time rate for each mode of transport considered, and transfer time for each mode of transport considered.

20. The method of claim 18, wherein the one or more physiological characteristics of the victim are age dependent or injury/condition specific.

* * * * *